(12) United States Patent
Zhong et al.

(10) Patent No.: US 9,955,694 B2
(45) Date of Patent: May 1, 2018

(54) EMULSIFIABLE CONCENTRATES OF INDOXACARB

(71) Applicant: Dow Global Technologies LLC, Midland, MI (US)

(72) Inventors: Ling Zhong, Shanghai (CN); Jianhai Mu, Shanghai (CN); Jing Ji, Shanghai (CN); Wei Lu, Shanghai (CN); Hua Ren, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 0 days. days.

(21) Appl. No.: 15/501,694

(22) PCT Filed: Aug. 5, 2014

(86) PCT No.: PCT/CN2014/083757
§ 371 (c)(1),
(2) Date: Feb. 3, 2017

(87) PCT Pub. No.: WO2016/019516
PCT Pub. Date: Feb. 11, 2016

(65) Prior Publication Data
US 2017/0223963 A1  Aug. 10, 2017

(51) Int. Cl.
*A01N 47/38* (2006.01)
*A01N 25/04* (2006.01)
(52) U.S. Cl.
CPC ............. *A01N 47/38* (2013.01); *A01N 25/04* (2013.01)
(58) Field of Classification Search
CPC ................................. A01N 47/38; A01N 25/04
See application file for complete search history.

(56) References Cited

U.S. PATENT DOCUMENTS

| 8,741,324 B2 | 6/2014 | Finch et al. |
| 2005/0032647 A1 | 2/2005 | Deckwer et al. |
| 2007/0184983 A1 * | 8/2007 | Finch .................... A01N 25/02 504/328 |
| 2010/0234227 A1 | 9/2010 | Thomas et al. |
| 2011/0195839 A1 | 8/2011 | Schlotterbeck et al. |
| 2016/0198716 A1 | 7/2016 | Pirotte |

FOREIGN PATENT DOCUMENTS

| CN | 101243798 | 8/2008 |
| CN | 101263819 | 9/2008 |
| CN | 101444220 | 6/2009 |
| CN | 101589720 | 12/2009 |
| CN | 101589723 | 12/2009 |
| CN | 101617651 | 1/2010 |
| CN | 101796959 | 8/2010 |
| CN | 102524283 | 7/2012 |
| CN | 102715152 | 10/2012 |
| CN | 102726373 | 10/2012 |
| WO | 2008069822 | 6/2008 |
| WO | 2017156751 | 9/2017 |

OTHER PUBLICATIONS

International Search Report & Written Opinion for related PCT Application PCT/CN2014/083757, dated Apr. 7, 2015 (9 pgs).

* cited by examiner

*Primary Examiner* — Sudhakar Katakam
(74) *Attorney, Agent, or Firm* — Brooks, Cameron & Huebsch, PLLC

(57) ABSTRACT

A formulation contains (a) 1-20 wt % of indoxacarb; (b) 10-30 wt % of a primary emulsifier mixture containing: (i) 1-15 wt % of a polyalkylene glycol having the following structure : $R^1O-(CH_2CH(CH_3)-O)_x-(CH_2CH_2O)_y-H$ where $R^1$ is a branched or linear alkyl having 4-16 carbons; x is a number from 0-11 and y is a number from 1-20; (ii) 5-15 wt % of an ethylene oxide/propylene oxide block copolymer hydroxyl terminated on both ends and having a molecular weight of 2000 to 8000 g/mol and an ethylene oxide moiety that is 40-60 wt % of total copolymer weight; and (iii) 1-10 wt % of sodium bisulfate adduct of bis (2-ethylhexyl) maleate; (c) 1-15 wt % of a non-aromatic methyl ester co-emulsifier; and (d) 10-70 wt % of a solvent consisting of cyclohexanone and at least one additional non-aromatic solvent; where the composition is fiee of aromatic solvents, amides, silicone containing components and azone.

8 Claims, No Drawings

EMULSIFIABLE CONCENTRATES OF INDOXACARB

This application is a National Stage Application under 35 U.S.C. § 371 of International Application Number PCT/CN2014/083757, filed Aug. 5, 2014 and published as WO 2016/019516 on Feb. 11, 2016, the entire contents of which are incorporated herein by reference in its entirety.

BACKGROUND OF THE INVENTION

Field of the Invention

The present invention relates to a concentrate formulation of indoxacarb.

Introduction

Indoxacarb is an oxadiazine based insecticide. It works by killing a pest by inhibiting sodium ion entry into nerve cells, resulting in paralysis and subsequent death of the pest. Indoxacarb is available as a pesticide or insecticidal formulation in the form of an emulsifiable concentrate (EC), suspension concentrate (SC) and water dispersible granular (WDG). EC forms of Indoxacarb are the most popular. However, EC forms of Indoxacarb typically contain aromatic solvents such as benzene, toluene, xylene, naphthalene and ethylbenzene. These solvents are used to dissolve the indoxacarb active. It is desirable to avoid use of aromatic solvents due to a perception that they can be harmful to the environment. However, forming an EC formulation of indoxacarb without aromatic solvents is challenging.

It is desirable to identify an EC formulation for indoxacarb that provides a stable emulsion and stable dilution of indoxacarb without the need for aromatic solvents.

BRIEF SUMMARY OF THE INVENTION

The present invention provides a solution to the problem of obtaining an emulsifiable concentrate of indoxacarb that provides a stable emulsion and stable dilution of indoxacarb without the need for aromatic solvents.

The present invention is a result of discovering a particularly emulsifier package that is capable of providing emulsion stability and dilution stability of indoxacarb without the need for aromatic solvents, or even typically used polar organic solvents such as dimethylformamide (DMF) or methanol.

In a first aspect, the present invention is a formulation comprising: (a) one to twenty weight percent of indoxacarb; (b) ten to thirty weight-percent of a primary emulsifier mixture comprising a combination of components (i), (ii) and (iii): (i) one to 15 weight-percent of a polyalkylene glycol selected from those having the following structure:

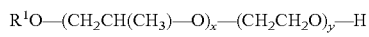

where $R^1$ is a branched or linear alkyl having 4-16 carbons; x is a number in a range of 0-11 and y is a number in a range of 1-20; (ii) five to fifteen weight-percent of an ethylene oxide/propylene oxide block copolymer that is hydroxyl terminated on both ends and that is characterized by having a molecular weight in a range of 2000 to 8000 and an ethylene oxide moiety weight that is 40-60 weight-percent of the total copolymer weight; (iii) one to ten weight-percent of sodium bisulfate adduct of bis(2-ethylhexyl) maleate; (c) one to fifteen weight-percent of a non-aromatic methyl ester co-emulsifier; and (d) ten to seventy weight-percent of a solvent consisting of cyclohexanone and one or more than one additional non-aromatic solvent; where weight-percent is relative to total formulation weight unless otherwise stated and wherein the composition is free of aromatic solvents, amides, silicone containing components and azone.

In a second aspect, the present invention is a method for preparing the formulation of the first aspect, the method comprising dissolving the indoxacarb into a combination of cyclohexanone and one or more than one additional non-aromatic solvent to form a mixture and then combining the mixture with the remaining components of the formulation.

The present invention is useful for providing the pesticide indoxacarb in concentrate form for use in exterminating pests.

DETAILED DESCRIPTION OF THE INVENTION

"And/or" means "and, or alternatively". All ranges include endpoints unless otherwise stated. Weight-percent (wt %) herein is relative to total formulation weight unless otherwise specified.

Test methods refer to the most recent test method as of the priority date of this document unless a date is indicated with the test method number as a hyphenated two digit number. References to test methods contain both a reference to the testing society and the test method number. Test method organizations are referenced by one of the following abbreviations: ASTM refers to ASTM International (formerly known as American Society for Testing and Materials); EN refers to European Norm; DIN refers to Deutsches Institut für Normung; CIPAC refers to Collaborative International Pesticides Analytical Council, and ISO refers to International Organization for Standards.

The formulation comprises indoxacarb at a concentration of one weight-percent (wt %) or more, preferably five wt % or more and can be ten wt % or more, 12 wt % or more, even 15 wt % or more and at the same time is typically 20 wt % or less and can be 18 wt % or less, 16wt % or less, 14 wt % or less, 12 wt % or less ten wt % or less and even 8 wt % or less. Indoxacarb serves as a pesticide ingredient in the formulation. Other pesticide ingredients can be present in addition to indoxacarb or the formulation can be free from pesticides other than indoxacarb.

The formulation further comprises a primary emulsifier mixture that has been found to stabilize the emulsion concentrate of indoxacarb in an absence of aromatic solvents. The primary emulsifier mixture is present at a concentration of ten weight percent or more and can be present at a concentration of 12 wt % or more, 14 wt % or more, 15 wt % or more, 16 wt % or more, 17 wt % or more, 18 wt % or more even 20 wt % or more while at the same time is present at a concentration of 30 wt % or less, preferably 28 wt % or less and can be present at a concentration of 25 wt % or less, 23 wt % or less, 22 wt % or less, 21 wt % or less even 20 wt % or less.

The primary emulsifier mixture comprises, or consists, of sodium bisulfate adduct of bis(2-ethylhexyl) maleate, a polyalkylene glycol having a particular structure and an ethylene oxide/propylene oxide block copolymer.

The sodium bisulfate adduct of bis(2-ethylhexyl) maleate is present at a concentration of one wt % or more, preferably two wt % or more and can be three wt % or more, five wt % or more, even seven wt % or more while at the same time typically being ten wt % or less, even nine wt % or less or eight wt % or less.

The polyalkylene glycol is selected from those having the following structure (I):

Where: $R^1$ is a branched or linear alkyl having four carbons or more, preferably six carbons or more, eight carbons or more, ten carbons or more and can have 12 carbons or more while at the same time has 16 carbons or fewer and can have 14 carbons or fewer or 12 carbons or fewer; x is a number in a range of 0-11 and can be one or more, two or more, three or more, four or more, five or more, even six or more while at the same time can be ten or less, even eight or less, seven or less, even six or less; and y is a number in a range of 1-20 and can be two or more, three or more, four or more, five or more, six or more, seven or more eight or more, nine or more, ten or more, 12 or more, 14 or more even 16 or more while at the same time can be 18 or less, 16 or less, 14 or less, 12 or less, ten or less, nine or less, eight or less, seven or less, six or less even five or less.

The polyalkylene glycol is typically present at a concentration of one wt % or more, preferably two wt % or more and can be present at a concentration three wt % or more, four wt % or more five wt % or more six wt % or more, seven wt % or more even eight wt % or more while at the same time is present at a concentration of 15 wt % or less and can be present at a concentration of 12 wt % or less, 10 wt % or less, eight wt % or less, seven wt % or less, six wt % or less even six wt % or less.

The ethylene oxide/propylene oxide block copolymer is hydroxyl terminated on both ends. That is, it has the following general structure (II):

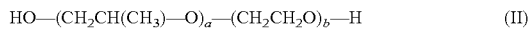

$$HO-(CH_2CH(CH_3)-O)_a-(CH_2CH_2O)_b-H \quad (II)$$

The values for a and b are selected so that: (a) the ratio of ethylene oxide moiety (that is, the ($CH_2CH_2O$) component) is 40 wt % or more, and can be 45 wt % or more even 50 wt % or more while at the same time is 60 wt % or less and can be 55 wt % or less even 50 wt % or less based on the total weight of the ethylene oxide/propylene oxide copolymer; and (b) the copolymer has a molecular weight of 2000 grams per mole (g/mol) or more, preferably 2500 g/mol or more and at the same time 8000 g/mol or less, preferably 6500 g/mole or less. Determine molecular weight for polyalkylene glycol polymers in grams per mole (g/mol) from the OH (hydroxyl) number according to ASTM D4274.

The ethylene oxide/propylene oxide copolymer is a block copolymer as opposed to a random copolymer. Experimental data reveals a random copolymer does not result in a formulation that is suitably stable while use of a block copolymer does produce a stable formulation.

In addition to the indoxacarb and primary emulsifier mixture, the present formulation comprises a non-aromatic methyl ester co-emulsifier. Suitable co-emulsifiers include methyl esters of carboxylic acids having 8 or more and can have 10 or more, 12 or more, 14 or more, 16 or more even 18 or more carbon atoms while at the same time typically have 24 or fewer, preferably 22 or fewer, 20 or fewer, 18 or fewer and can have 16 or fewer, 14 or fewer, 12 or fewer even 10 or fewer carbons. Examples of suitable methyl ester co-emulsifiers include one or more than one selected from a group consisting of methyl oleate, methyl ester of soybean oil, methyl octanoate and methyl decanoate.

The methyl ester co-emulsifier is present in the formulation at a concentration of one wt % or more, preferably two wt % or more, more preferably four wt % or more and can be present at a concentration of six wt % or more while at the same time is present at a concentration of 15 wt % or less, preferably 12 wt % or less, more preferably ten wt % or less and can be eight wt % or less.

The formulation of the present invention further comprises a solvent consisting of cyclohexanone and one or more than one additional non-aromatic solvent. "Solvent" herein refers to a liquid in which indoxacarb is soluble at 23° C. and 101 kiloPascals pressure. Examples of suitable additional non-aromatic solvents include those selected from a group consisting of N-methyl pyrrolidone, gamma-butyrolactone, isophorone, dipropylene glycol methyl ether acetate, propylene glycol phenyl ether, butyl carbitol, hexyl carbitol, ethylene glycol-N-hexyl ether, and butoxyrtriglycol. Desirably, the formulation includes cyclohexanone and gamma-butyrolactone.

Unlike other emulsion concentrate formulations of indoxacarb, the present formulation does not require and can be free of any one or any combination of more than one of the following: aromatic solvents, methanol, dimethylformamide, amides, silicone containing components, laurocapram ("azone"), urea resin, and antifreeze materials (for example, ethylene alcohol, propylene glycol, propanetriol and carbamide).

The formulation of the present invention is an emulsion concentrate and can be in the form of a microemulsion.

It is possible to prepare the formulation of the present invention by dissolving the indoxacarb into the cyclohexanone, an additional non-aromatic solvent, or a combination of cyclohexanone and an additional non-aromatic solvent and then adding the remaining components of the formulation together. If there are additional pesticides in the formulation, it is desirable to dissolve those into the cylcohexanone, additional non-aromatic solvent, or combination of cyclohexanone and additional non-aromatic solvent with the indoxacarb. It is desirable to mix the components during the dissolving step and when adding the remaining formulation components. After mixing thoroughly, it is desirable to filter the resulting mixture to remove undissolved impurities in order to yield what is typically a clear formulation.

It is desirable and typical for the formulation of the present invention to have any one or any combination of more than one, and preferably has all of the following characteristics:

Clarity. A clear liquid, pH in a range of four to seven as determined by standard method CIPAC MT75.

Water Content. Less than 0.5 wt % water content as determined by standard test method CIPAC MT 30.1. Measure water content using Metrohm Karl Fischer Water Content Tester.

Hard Water Test. No oil slick or crystal separation in hard water testing according to standard methods CIPAC 36.1, 36.2, and 36.3. Dilute the formulation with standard hard water in a 100 milliliter graduated cylinder using a dilution ratio of 20-200 times. After dilution, place the sample in a water bath for two hours at 30° C. Observe for oil slick and precipitate formation in the formulation. Standard hard water is made by dissolving anhydrous calcium chloride (0.304 grams) and magnesium chloride hexahydrate (0.139 g) in deionized water and dilute to scale in a 1000 milliliter volumetric flask.

Low Temperature Storage Stability. Pass a low temperature storage stability testing according to standard test method CIPAC MT 39.3. Place 100 milliliters of formulation in an incubator at zero degrees Celsius (° C.) for one hours. If there is no solid or oily matter visible, keep the formulation in the incubator for seven days. Remove sample and place at approximately 23° C. for three hours, centrifuge for 15 minutes and measure the volume of precipitate. Precipitate should be less than 0.3 milliliters to pass the test.

Heat Storage Stability. Pass a heat storage stability testing according to CIPAC MT 46.3. Store the formulation at 54° C. for two weeks. There should be no oil slick or precipitate. The heat-treated sample should also pass the hard water test.

EXAMPLES

Table 1 discloses the components used in preparing the examples below.

TABLE 1

| Component | Description |
|---|---|
| Emulsifier 1 | Structure (I) where $R^1$ is a linear 12-14 carbon alkyl, x is zero and y is 5. Commercially available under the trade name TERGITOL ™ 15-S-15. (TERGITOL is a trademark of Union Carbide Corporation) |
| Emulsifier 2 | Structure (II) block copolymer with 6500 g/mol molecular weight and 50 wt % ethylene oxide moiety. Commercially available as DOWFAX ™ D-850 (DOWFAX is a trademark of The Dow Chemical Company). |
| Emulsifier 3 | Sodium bisulfate adduct of bis(2-ethylhexyl) maleate. Commercially available under the trade name TRITON ™ GR-7M (TRITON is a trademark of The Dow Chemical Company) |
| Emulsifier 4 | Structure (I) where $R^1$ is a linear 8 carbon alkyl, x is 5 and y is 6. Commercially available as ECOSURF ™ EH-6 (ECOSURF is a trademark of The Dow Chemical Company). |
| Emulsifier 5 | Structure (II) block copolymer with 3850 g/mol molecular weight and 43 wt % ethylene oxide moiety. Commercially available under the trade name TERGITOL ™ XD. |
| Emulsifier 6 | Structure (I) where $R^1$ is a linear 8 carbon alkyl, x is 5 and y is 3. Commercially available under the trade name ECOSURF ™ EH-3. |
| Emulsifier 7 | Structure (II) block copolymer with 4190 g/mol molecular weight and 17 wt % ethylene oxide moiety. Commercially available under the trade name TERGITOL L-101. |
| Emulsifier 8 | A random copo0lymer of ethylene oxide and propylene oxide having a molecular weight of 390 g/mol and containing 50 wt % ethylene oxide moiety. Commercially available under the trade name UCON ™ 50HB5100. (UCON is a trademark of Union Carbide Corporation) |
| Co-emulsifier 1 | Methyl octanoate |
| Co-emulsifier 2 | Methyl decanoate |

Prepare the following examples dissolving the actives into a mixture of the solvents by mixing together at 45-55° C. for 1-2 hours until the actives dissolve to form a mixture. Then add emulsifier and co-emulsifier into the mixture and continue mixing at 45-55° C. for approximately 0.5 hours to dissolve the components. Filter the resulting mixture with qualitative filter paper (Type 101, which complies with GB/T 1914-2007) to remove insoluble impurities. In each case, the resulting mixture is clear. Subject the resulting mixture to the Water Content, Hard Water Test, Low Temperature Storage Stability and Heat Storage tests described above. Results are reported below.

Example 1

| Component | Identity | Wt % of Formulation |
|---|---|---|
| Active | Indoxacarb | 7 |
| Solvent | Cyclohexanone | 4 |
| Solvent | N-methyl pyrrolidone | 47 |
| Solvent | gamma-butyrolactone | 8 |
| Emulsifier | Emulsifier 1 | 10 |
| Emulsifier | Emulsifier 2 | 10 |
| Emulsifier | Emulsifier 3 | 10 |
| Co-emulsifier | Co-emulsifier 1 | 4 |

Example 1 is clear, has a pH of 5.79, has a water content 0.23 wt %, and passes each of the Hard Water Test, Low Temperature Storage Stability test and Heat Storage Stability test.

Example 2

| Component | Identity | Wt % of Formulation |
|---|---|---|
| Active | Indoxacarb | 4 |
| Active | Avermectin | 2 |
| Solvent | Cyclohexanone | 8 |
| Solvent | N-methyl pyrrolidone | 40 |
| Solvent | gamma-butyrolactone | 16 |
| Emulsifier | Emulsifier 1 | 7 |
| Emulsifier | Emulsifier 2 | 7 |
| Emulsifier | Emulsifier 3 | 7 |
| Co-emulsifier | Co-emulsifier 1 | 9 |

Example 2 is clear, has a pH of 5.75, has a water content0.25 wt %, and passes each of the Hard Water Test, Low Temperature Storage Stability test and Heat Storage Stability test.

Example 3

| Component | Identity | Wt % of Formulation |
|---|---|---|
| Active | Indoxacarb | 12 |
| Active | Acetamiprid | 4.5 |
| Solvent | Cyclohexanone | 6.8 |
| Solvent | N-methyl pyrrolidone | 36.8 |
| Solvent | gamma-butyrolactone | 14.3 |
| Solvent | Ethanol | 2.8 |
| Emulsifier | Emulsifier 4 | 5 |
| Emulsifier | Emulsifier 5 | 5 |
| Emulsifier | Emulsifier 3 | 5 |
| Co-emulsifier | Co-emulsifier 2 | 7.7 |

Example 3 is clear, has a pH of 5.94, has a water content 0.16 wt %, and passes each of the Hard Water Test, Low Temperature Storage Stability test and Heat Storage Stability test.

Comparative Example A

| Component | Identity | Wt % of Formulation |
|---|---|---|
| Active | Indoxacarb | 16 |
| Solvent | N-methyl pyrrolidone | 37.5 |
| Solvent | gamma-butyrolactone | 15 |
| Solvent | Cyclohexanone | 7.5 |
| Emulsifier | Emulsifier 6 | 5 |
| Emulsifier | Emulsifier 4 | 5 |
| Emulsifier | Emulsifier 5 | 5 |
| Co-emulsifier | Co-emulsifier 2 | 9.9 |

Comparative Example A lacks sodium bisulfate adduct of bis(2-ethylhexyl) maleate and so falls outside the scope of the present invention. Comparative Example A lacks hard water dilution stability and showed crystal formation within one hour of the hard water test.

Comparative Example B

| Component | Identity | Wt % of Formulation |
|---|---|---|
| Active | Indoxacarb | 16 |
| Solvent | N-methyl pyrrolidone | 37.5 |
| Solvent | gamma-butyrolactone | 15 |
| Solvent | Cyclohexanone | 7.5 |
| Emulsifier | Calcium dodecylbenzene sulfonate | 5 |
| Emulsifier | Emulsifier 4 | 5 |
| Emulsifier | Emulsifier 5 | 5 |
| Co-emulsifier | Co-emulsifier 2 | 9.9 |

Comparative Example B lacks sodium bisulfate adduct of bis(2-ethylhexyl) maleate and therefore falls outside the scope of the present invention, but includes an alternative anionic surfactant. Comparative Example B still lacks hard water dilution stability and showed crystal formation within one hour of the hard water test.

Comparative Example C

| Component | Identity | Wt % of Formulation |
|---|---|---|
| Active | Indoxacarb | 16 |
| Solvent | Cyclohexanone | 7.5 |
| Solvent | N-methyl pyrrolidone | 37.5 |
| Solvent | gamma-butyrolactone | 15 |
| Emulsifier | Nonyl phenol ethoxylate | 5 |
| Emulsifier | Emulsifier 2 | 5 |
| Emulsifier | Emulsifier 3 | 5 |
| Co-emulsifier | Co-emulsifier 2 | 9 |

Comparative Example C lacks the required polyalkylene glycol component of the primary emulsifier and so falls outside the scope of the present invention. Comparative Example C is clear, but fails to pass the Hard Water Test due to crystal formation within one hour.

Comparative Example D

| Component | Identity | Wt % of Formulation |
|---|---|---|
| Active | Indoxacarb | 16 |
| Solvent | Cyclohexanone | 7.5 |
| Solvent | N-methyl pyrrolidone | 37.5 |
| Solvent | Hydrocarbon solvent | 15 |
| Emulsifier | Emulsifier 4 | 5 |
| Emulsifier | Emulsifier 7 | 5 |
| Emulsifier | Emulsifier 3 | 5 |
| Co-emulsifier | Co-emulsifier 2 | 9 |

Comparative Example D lacks the required ethylene oxide/propylene oxide copolymer of the primary emulsifier and so falls outside the scope of the present invention. Comparative Example D fails to pass the Hard Water Test due to crystal formation within one hour.

Comparative Example E

| Component | Identity | Wt % of Formulation |
|---|---|---|
| Active | Indoxacarb | 16 |
| Solvent | Cyclohexanone | 7.5 |
| Solvent | N-methyl pyrrolidone | 37.5 |
| Solvent | gamma-butyrolactone | 15 |
| Emulsifier | Emulsifier 1 | 5 |
| Emulsifier | Emulsifier 8 | 5 |
| Emulsifier | Emulsifier 3 | 5 |
| Co-emulsifier | Co-emulsifier 2 | 9 |

Comparative Example E uses a random copolymer rather than a block copolymer for the ethylene oxide/propylene oxide copolymer of the primary emulsifier and so falls outside the scope of the present invention. Comparative Example E fails to form a stable emulsion and shows separation after 15 minutes of storage.

What is claimed is:
1. A formulation comprising:
(a) one to twenty weight-percent of indoxacarb;
(b) ten to thirty weight-percent of a primary emulsifier mixture comprising a combination of components (i), (ii) and (iii):
(i) one to 15 weight-percent of a polyalkylene glycol selected from those having the following structure:

$$R^1O-(CH_2CH(CH_3)-O)_x-(CH_2CH_2O)_y-H$$

where $R^1$ is a branched or linear alkyl having 4-16 carbons; x is a number in a range of 0-11 and y is a number in a range of 1-20;
(ii) five to fifteen weight-percent of an ethylene oxide/propylene oxide block copolymer that is hydroxyl terminated on both ends and that is characterized by having a molecular weight in a range of 2000 to 8000 and an ethylene oxide moiety weight that is 40-60 weight-percent of the total copolymer weight;
(iii) one to ten weight-percent of sodium bisulfate adduct of bis(2-ethylhexyl) maleate;
(c) one to fifteen weight-percent of a non-aromatic methyl ester co-emulsifier; and
(d) ten to seventy weight-percent of solvent consisting of cyclohexanone and one or more than one additional non-aromatic solvent;

where weight-percent is relative to total formulation weight unless otherwise stated and wherein the composition is free of aromatic solvents, amides, silicone containing components and azone.

2. The formulation of claim 1, further characterized by $R^1$ containing 8-10 carbons.

3. The formulation of claim 1, further characterized by x and y independently being a number in a range of one to 6.

4. The formulation of claim 1, further characterized by the co-emulsifier (c) being selected from methyl esters of carboxylic acids having from 8-10 carbons.

5. The formulation of claim 1, further characterized by being free of antifreeze materials selected from a group consisting of ethylene alcohol, propylene glycol, propanetriol and carbamide.

6. The formulation of claim 1, further characterized by the composition being in the form of a microemulsion.

7. The formulation of claim 1, further characterized by the composition being free of urea resin prepolymer.

8. A method for preparing the formulation of any previous claim, the method comprising dissolving the indoxacarb into a combination of cyclohexanone and one or more than one additional non-aromatic solvent to form a mixture and then combining the mixture with the remaining components of the formulation.

* * * * *